United States Patent
Sessions et al.

[11] Patent Number: 6,043,406
[45] Date of Patent: Mar. 28, 2000

[54] THIN FILM WOUND DRESSING AND METHOD FOR MAKING SAME

[75] Inventors: Robert W. Sessions, Burr Ridge; Rainer Schmeichel, Glen Ellyn, both of Ill.

[73] Assignee: Ferris Mfg, Corp., Burr Ridge, Ill.

[21] Appl. No.: 09/032,144

[22] Filed: Feb. 27, 1998

[51] Int. Cl.⁷ .................................................. A61F 13/00
[52] U.S. Cl. ................................ 602/41; 602/57; 602/58
[58] Field of Search .................... 602/41, 57, 58; 128/155

[56] References Cited

U.S. PATENT DOCUMENTS

| | | | |
|---|---|---|---|
| 2,958,437 | 11/1960 | Mengis | 216/25 |
| 2,995,174 | 8/1961 | Wang | 154/1.6 |
| 3,017,795 | 1/1962 | Joa | 83/129 |
| 3,140,572 | 7/1964 | Petersen et al. | 53/28 |
| 3,495,992 | 2/1970 | De For | 99/171 |
| 3,773,591 | 11/1973 | Blair | 156/265 |
| 4,216,046 | 8/1980 | Hackert | 156/252 |
| 4,334,530 | 6/1982 | Hassell | 128/156 |
| 4,436,576 | 3/1984 | Seiden | 156/543 |
| 4,455,809 | 6/1984 | Dallaserra | 53/435 |
| 4,485,809 | 12/1984 | Dellas | 128/156 |
| 4,499,896 | 2/1985 | Heinecke | 128/156 |
| 4,507,162 | 3/1985 | Iwamoto | 156/157 |
| 4,525,229 | 6/1985 | Suzuki et al. | 156/161 |
| 4,600,001 | 7/1986 | Gilman | 128/156 |
| 4,609,556 | 9/1986 | Goedert | 426/394 |
| 4,619,253 | 10/1986 | Anhauser et al. | 218/156 |
| 4,630,426 | 12/1986 | Gentry | 53/428 |
| 4,787,380 | 11/1988 | Scott | 128/156 |
| 4,884,563 | 12/1989 | Sessions | 128/155 |
| 4,915,102 | 4/1990 | Kwiatek et al. | 128/156 |
| 4,926,850 | 5/1990 | Lott et al. | 128/155 |
| 5,021,111 | 6/1991 | Swenson | 156/264 |
| 5,137,766 | 8/1992 | Mazanek et al. | 428/68 |
| 5,415,627 | 5/1995 | Rasmussen et al. | 602/57 |
| 5,423,737 | 6/1995 | Cartmell et al. | 602/57 |
| 5,437,622 | 8/1995 | Carion | 602/57 |
| 5,489,262 | 2/1996 | Cartmell et al. | 602/57 |
| 5,501,661 | 3/1996 | Cartmell et al. | 602/58 |
| 5,520,629 | 5/1996 | Heinecke et al. | 602/57 |

OTHER PUBLICATIONS

Ferris Mfg. Corp. undated 2 pages describing Ferris Poly-Mem Dressings—A total wound care system.
Ferris Mfg. Corp. undated 2 pages describing Ferris Poly-Mem Surgical Dressings.
Sep./Oct. 1996 page from "Wound Care Patent Newsletter" on Bandages/Dressings.

*Primary Examiner*—John G. Weiss
*Assistant Examiner*—Kelvin Hart
*Attorney, Agent, or Firm*—Leydig, Voit & Mayer, Ltd.

[57] ABSTRACT

A non-stretching wound dressing is provided for use with a patient. The wound dressing includes a cover sheet having top and bottom sides, a thin film sheet formed on the bottom side of the cover sheet, the film sheet having first and second ends and an adhesive side, and a carrier sheet in adjacent contact with the adhesive side of the thin film sheet. The dressing also includes a first gripping tab attached to one end of the thin film sheet and disposed between the film sheet and the carrier sheet for separating the carrier sheet from the film sheet with the cover sheet remaining affixed to the film sheet. A second gripping tab is attached to the top side of the cover sheet and at one end of the cover sheet so that pulling on the second gripping tab releases the cover sheet from the film sheet with the film sheet remaining in place on the patient. An intermediate liner is attached to the adhesive side of the film sheet and disposed between the film sheet and the carrier sheet to promote removal of the film sheet and the carrier sheet, and to permit the wound dressing to be held by the first gripping tab and intermediate liner without contacting the thin film sheet. In one embodiment, the thin film sheet has a thickness of less than about 1.0 mil, more preferably, less than about 1.0 mil and most preferably, less than about 0.75 mil.

22 Claims, 3 Drawing Sheets

THIN FILM WOUND DRESSING AND METHOD FOR MAKING SAME

FIELD OF THE INVENTION

The present invention relates to wound dressings and methods for making such wound dressings and, in particular, to a thin film wound dressing which can be applied to a patient without stretching, and a method for the continuous production of a large number of such wound dressings.

BACKGROUND OF THE INVENTION

Wound dressings, consisting of a urethane film having adhesive on one side for carrying an absorbent pad and adhering to a patient's skin surrounding an open wound, are known in the art. The flexible nature of the urethane film permits the dressing to conform to virtually any contour of the patient's skin at the location where the dressing is applied. The flexibility and thinness of the urethane film, however, present the problem of applying the wound dressing to the patient without stretching the urethane film. Stretching of the dressing prior to or during application to a patient may momentarily expand the stretchable urethane film and, even though the dressing may appear smooth when applied to the patient it will very quickly contract after the stretching forces are relieved, thereby causing discomfort to the patient and irritation to the area surrounding the wound. On weak or damaged skin, as in the elderly, the stretching forces may even cause abscesses or other skin damage.

One proposed solution to the stretching problem has been to use heavier or thicker urethane films. Unfortunately, heavier urethane films are undesirable as a wound dressing due to decreased flexibility and less gas permeability. Many conventional urethane films are about 1.0 mil or more thick. Although thinner urethane films will achieve greater gas permeability, moisture vapor transmission rates and increased flexibility and comfort, use of such thin films has been unsuccessful because they are relatively fragile and consequently difficult to work with during manufacture and assembly of the wound dressing.

Another proposed solution to this problem is to attach a flexible but non-stretching backing sheet to the urethane film using adhesive. The backing sheet remains in contact with the urethane film while the dressing is being applied to the patient, thereby eliminating stretching during application of the dressing. After the wound dressing has been attached to the patient, the backing sheet is subsequently peeled from the urethane film. Unfortunately, methods using adhesive to attach the urethane film to conventional backing sheets have been unable to handle the fragile and thin urethane films.

Another problem encountered when applying the polyurethane film to the wound is maintaining the sterility of the dressing during the application process. Previous products such as a polyurethane film wound dressings Ensure-IT (Deseret Medical, Inc.) and POLYSKIN® transparent dressing (Kendall Company, Boston, Mass.) required contact between fingers and the adhesive surface of the polyurethane film during application. It will be appreciated that such contact is undesirable as it may potentially contaminate the urethane film.

OBJECTS AND SUMMARY OF THE INVENTION

In view of the foregoing, it is an object of the present invention to provide a wound dressing which provides ease of application while maintaining sterility of the urethane film and the absorbent pad.

Another object of the invention is to provide a tab system that allows support of the non-stretchable wound dressing following removal of the carrier sheet. A related object is to provide a wound dressing having a tab system that allows manipulation of the wound dressing without contaminating contact between the sterile urethane film and the user's fingers.

One object of the invention is to provide a wound dressing having a tab system that permits application of the wound dressing with one hand.

Yet another object of the invention is the coding of the tabs to indicate the sequential order of utilization of the tabs.

Still another object of the present invention is to provide a wound dressing having a unique thin urethane film which enhances healing and maximizes gas permeability with the patient's skin. A more specific object is to provide a thin urethane film having a thickness of about 1.0 mil or less.

It is an object of the present invention to provide a thin film, non-stretchable wound dressing which can be manufactured by overlying a series of continuous strips.

In accordance with these objects, the present invention provides a non-stretchable wound dressing consisting of a thin film of material such as polyurethane which is less than about 1.0 mil thick, more preferably about 0.75 mils thick, and most preferably less than about 0.75 mil thick. The wound dressing has a non-stretchable cover sheet, such as MYLAR®, onto which the urethane film is cast.

The urethane film has an adhesive side and first and second releasable ends. The adhesive side of the first releasable end receives a first gripping tab, which extends outboard of the left releasable end of the cover sheet. The cover sheet and first gripping tab are in adjacent contact with each other but are not adhesively attached so that they may be freely separated from each other. A second gripping tab may be attached to the other side of the urethane film. The adhesive side of the second releasable end receives an intermediate liner. An absorbent pad is centrally positioned on the urethane film. Finally, a carrier sheet is attached to the urethane film surrounding the pad, thereby covering and protecting the sterility of the pad.

In order to apply the wound dressing, the user pulls the first gripping tab which lifts the combination urethane film/cover sheet from the release surface of the carrier sheet, thereby exposing the adhesive side of the urethane film. Holding the first tab and, if necessary, the intermediate liner end to prevent the user's fingers from contacting the urethane film or absorbent pad, the user places this layered sheet combination over the wound. The cover sheet prevents the urethane sheet from stretching while permitting the urethane film to contact and conform to the contours of the patient's skin. After the combination urethane film/cover sheet has been placed over the wound, the second gripping tab may be peeled away from the other side of the urethane film without stretching or wrinkling thereof. The first and second releasable ends may then be removed, leaving the wound dressing in proper contact with the patient's skin.

An object of the invention is to provide a method of manufacturing wound coverings incorporating thin urethane films. In a preferred embodiment, the thin urethane films are less than about 1.0 thick and in a more preferred embodiment, about 0.75 mils thick.

DESCRIPTION OF THE DRAWINGS

FIG. 4 shows the carrier sheet being peeled away from the layered wound dressing and cover sheet.

FIG. 5 shows the adhesive side of the urethane film placed in adjacent contact with the patient's skin and the cover sheet being peeled away from the urethane film.

FIG. 6 shows the ends of the urethane film being pulled away from the finished wound dressing.

FIG. 7 shows a tri-layered sheet consisting of a cover sheet, a thin urethane film, and an intermediate liner.

FIG. 8 shows the urethane film after removal of a portion of the left urethane end and a portion of the intermediate liner, and formation of the urethane first and second releasable ends.

FIG. 9 shows the absorbent pad attached to the adhesive side of the urethane film.

FIG. 10 shows the first gripping tab attached to the adhesive side of the first releasable end of the urethane film.

FIG. 11 shows the carrier sheet being positioned into contact with the adhesive side of the urethane film, and the second tab attached to the cover sheet.

While the invention will be described and disclosed in connection with certain preferred embodiments and procedures, it is not intended to limit the invention to those specific embodiments. Rather, it is intended to cover all such alternative embodiments and modifications as fall within the spirit and scope of the invention.

DESCRIPTION OF THE PREFERRED EMBODIMENTS

Figure 1:
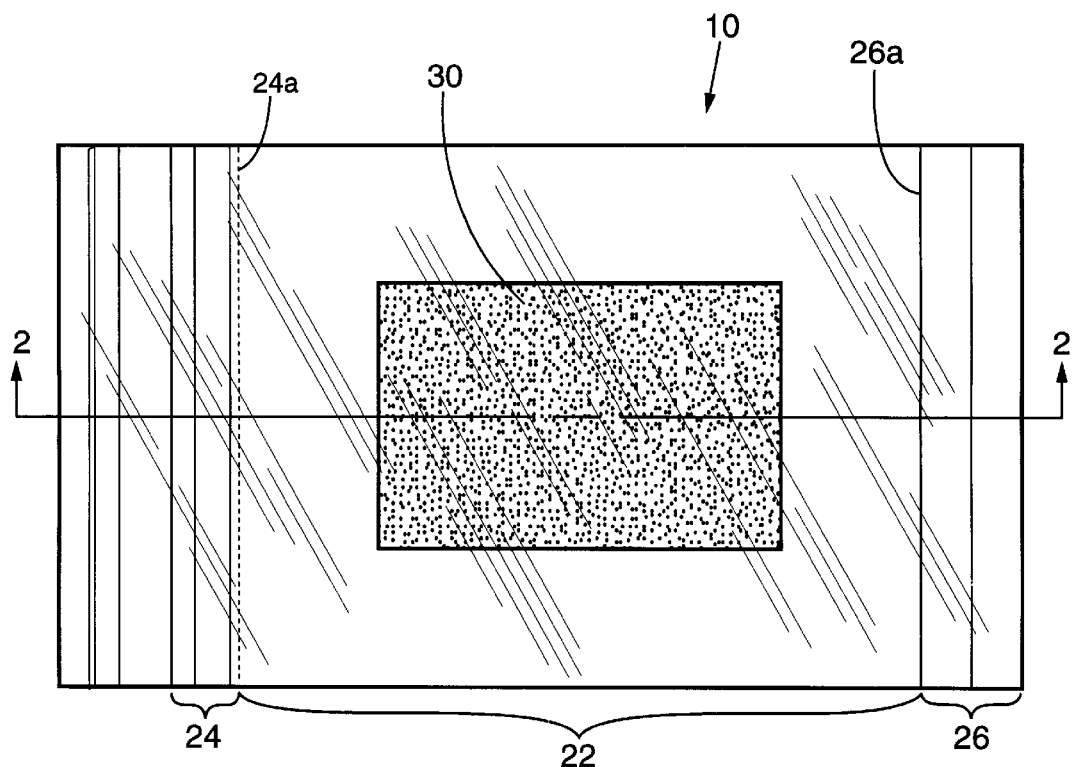
FIG. 1 is a top view of a wound dressing in accordance with the present invention.
Figure 2:
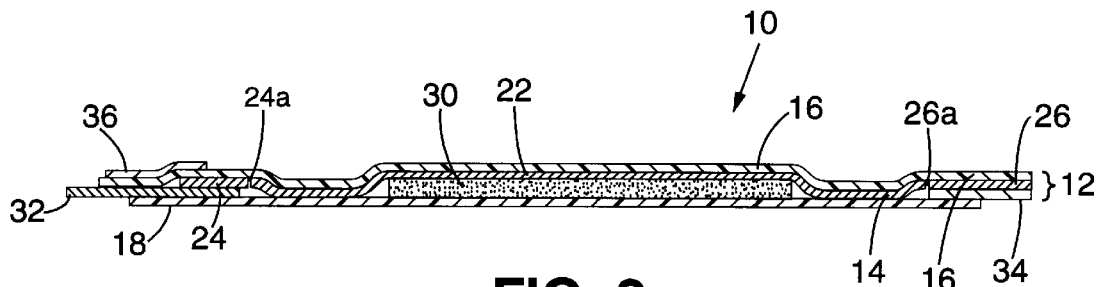
FIG. 2 is a cross-sectional view of the wound dressing taken along line 2—2 in FIG. 1.
Figure 3:
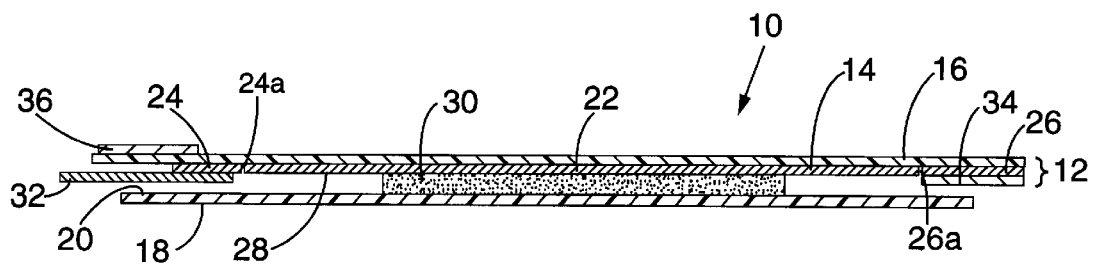
FIG. 3 is a partially exploded view of the wound dressing shown in FIG. 2.

Referring to the figures, and particularly to FIGS. 1–3, a wound dressing 10 is provided in accordance with the present invention. The wound dressing 10 consists of a substantially tri-layered sheet combination 12, the combination generally consisting of a middle urethane film 14 sandwiched between an upper cover sheet 16 and a bottom carrier sheet 18 which extend along substantially the entire length of the wound dressing 10.

The top layer of the wound dressing 10 is a non-stretchable but flexible cover sheet 16, which is sufficiently flexible so it does not interfere with the ability of the urethane film 14 to conform to the contour of the patient P. The cover sheet 16 may be comprised, for example, of MYLAR® polyester film, but other materials will be known to those skilled in the art.

The bottom layer of the wound dressing 10 consists of a carrier sheet or bottom liner 18. The carrier sheet 18 is preferably made of plastic, but in other embodiments may be made of relatively heavy paper. The bottom carrier sheet 18 has a release side 20 which has means for facilitating release of the urethane film 14 from the carrier sheet 18. In one embodiment, the release means comprises a silicon release coating on the release side 20, but other release means and treatments will be known in the art.

In accordance with certain objects of the present invention, the cover sheet 16 carries a thin urethane film 14 which is preferably less than about 1.0 mil thick, more preferably about 0.75 mil thick and, most preferably, less than about 0.75 mil thick. The thin urethane film 14 has a greater moisture vapor transmission rate (MVTR) than conventional relatively thick urethane films used in wound dressings of the type described herein. It will, of course, be appreciated that maximizing the MVTR enhances breathability of the wound dressing 10 and wound healing. The thin film 14 also conforms more effectively to the contour of a patient's skin and, once applied to the skin, more effectively flexes in response to movement of the patient's skin than conventional thick urethane films. The thin film is referred to as a "urethane" film, but other suitable materials are known in the art. In one embodiment, a suitable material for the film sheet may be urethane film (medical grade).

In order to handle the relatively fragile thin urethane film 14 during manufacture, the urethane film 14 is preferably formed or cast directly on the cover sheet 16. Once cast on the cover sheet 16, the unitary cover sheet 16 and thin urethane film 14 may be used in subsequent manufacturing steps without stretching, tearing or otherwise destroying the thin urethane 14. Moreover, unlike many prior wound dressings, it is not necessary to separate the urethane film 14 from a conventional backing sheet or subsequently use adhesive to attach the cover sheet 16 and urethane film 14 together. When it is necessary, the cover sheet 16 and urethane film 14 may be removed simply by pulling the two layers apart, thereby overcoming the attractive forces which normally keep the two layers together.

Figure 8:
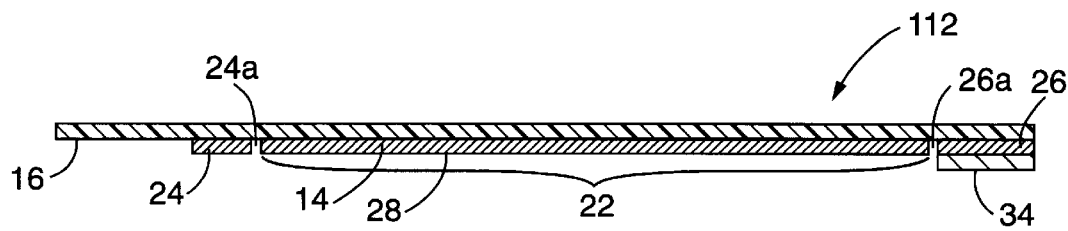
Figure 10:
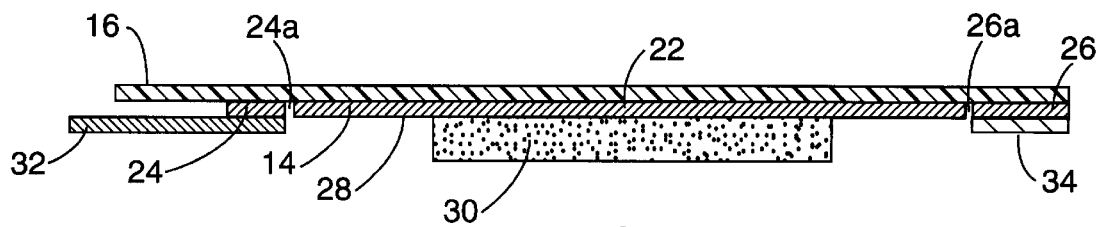

As best shown in FIG. 8, the urethane film 14 consists of a middle portion 22 and two releasable ends which will be generally referenced as first or left releasable end 24 and second or right releasable end 26. The urethane film 14 has an adhesive side 28 to which an appropriate conventional adhesive is applied. As best shown in FIGS. 1 and 10, the middle portion 22 is thus capable of receiving and carrying an absorbent pad 30 which is centrally disposed on the wound dressing 10. Referring to FIG. 1, it will be seen that the illustrated pad 30 has a generally rectangular shape centrally disposed in the middle of the middle portion 22. It will be appreciated that the outer periphery of the middle portion 22 remains uncovered so that the adhesive side 28 may engage the bottom carrier sheet 18, permitting the combination of the cover sheet 16/urethane film 14 to be releasably attached to the carrier sheet 18 as best shown in FIGS. 1–2.

Although the absorbent material 30 shown in the figures is rectangular, it may have any desirable shape including a square, circle, diamond, ellipse or the like. The absorbent material 30 may be gauze, sponge or other inert absorbent material which is suitable for absorbing moisture from the wound area. The presence of an absorbent material or a hydrophilic absorbent material patch not only serves as an absorbent, it also serves as an insulating material that holds the body's warmth at the wound site. This increased warmth due to the patch facilitates a more rapid healing of the wound. The absorbent material 30 may be clear or opaque to conceal the wound area. Among the hydrophilic absorbent materials which may be suitable are poly (D-Glucosamine) from Bentech Laboratories and ARASORB™ 720 superabsorbent polymer from Arakawa Chemical Inc., Chicago, Ill., and WATERLOCK™ A-222; A-100, D-212, D-242, G400 and WATERLOCK B, C and H from Grain Processing Corporation.

In other embodiments, the absorbent material 30 may contain medication. The medication may be an antibiotic, a healing promoting agent, an anti-inflammatory agent, a transdermal diffusable pharmaceutical, a coagulant or an anti-coagulant. Anticipated antibiotics include typical bacteriostatic and bactericidal agents, anti-fungal and anti-viral agents. Among the anti-bacterial agents and anti-fungal agents are the penicillins, streptomycins, sulfuramides, cephalosporins, kanamycins, gentaminicin, tobramycin, neomycin, paromomycin, chloramphenicol, tetracyclines, lincomycin, novobiocin, nalidixic acid, rifamycins, polymyxin B, griseofulvin, pimaricin, conystatin, amphotericin B; and for viruses rifamycin, nucleic acid analogs, arabinosylthymine, 5-iodo-5'amino-2'-5' dideoxycridine, arabinosyl adenine, arabinosyl cytosine, acycloguanosine, ribavirin, phosphono acetic acid, and idoxuridine. Among healing promoting agents are growth promoting hormones, among them epidermal growth factor and urogastrone. Among the anti-inflammatory agents are the corticosteroids. Among the transdermal diffusable pharmaceuticals are nitroglycerin, and other cardiac and blood pressure affecting agents. Among the coagulants are the blood clotting factors and activators of the intrinsic or extrinsic clotting pathways. Among the anti-coagulants are heparin, citric acid, protamine sulfate, and other inhibitors of blood clotting. Also useful as anti-blood clotting agents are thrombolytic enzymes such as streptokinase and urokinase.

Referring again to FIGS. 2–3, the adhesive side 23 of the left and right releasable ends 24, 26 are capable of receiving and carrying first tab 32 and an intermediate liner 34, respectively. The intermediate liner 34, disposed between the cover sheet 16 and the carrier sheet 18, covers substantially all of the right releasable end 26 so that the adhesive side 28 of the right releasable end 34 does not adhere to the carrier sheet 18. The first tab 32, which extends outboard of the left end of the cover sheet 16, is similarly disposed between the cover sheet 16 and the carrier sheet and covers substantially all of the left releasable end 24 so that the adhesive side 28 of the left end 24 does not adhere to the carrier sheet 18. The faces of the first tab 32 and the intermediate liner 34 in adjacent contact with the carrier sheet 18 do not carry an adhesive so that they do not adhere to the release side 20 of the carrier sheet 18.

Means is provided for removing the left and right releasable ends 24, 26 of the urethane film 14 after the wound dressing 10 is applied to a wound. In the illustrated embodiment, the left releasable end 24 is perforated along the first or left release line 24a and the right releasable end 26 is scored along the second or right release line 26a. Thus, the release lines 24a, 26a are substantially weaker than the remaining urethane film 14 and will tear away from the middle portion 22 of the urethane film 14. Generally, the perforated line 24a is slightly stronger than the scored line 26a so that scored line 26a will be removed first when the two releasable ends 24, 26 are simultaneously pulled with equal force. Of course, other methods may be used to permit removal of the two releasable ends 24, 26, including, for example, scoring or perforating both release lines.

A second gripping tab or strip 36 may be bonded at one end of the cover sheet 16 by any suitable adhesive. Referring to FIGS. 1–2, it will be seen that, in the illustrated embodiment, the second tab 36 and the left end of the cover sheet 16 are inboard of the first tab 32 so that first tab 32 may be more easily grasped by a user to separate the combination of the upper cover sheet 16/urethane film 14 from the bottom carrier sheet 18.

Figure 4:
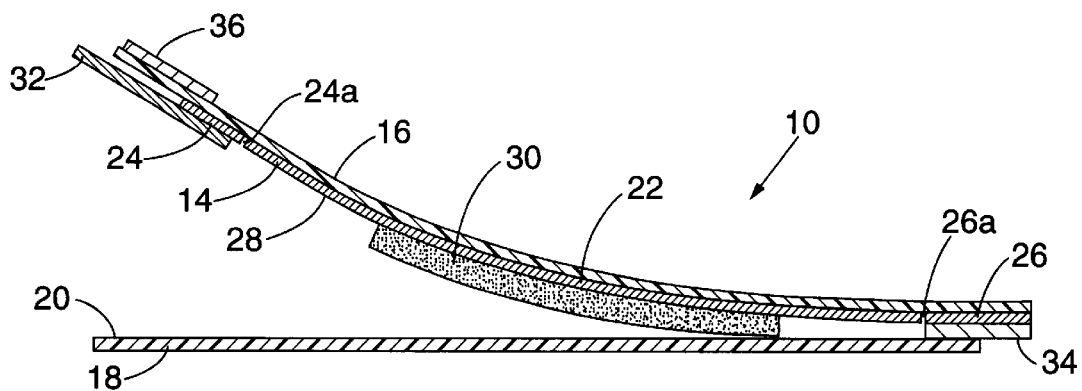
FIGS. 4–6 are sequential views showing the application of the wound dressing to a wound. Specifically.
Figure 5:
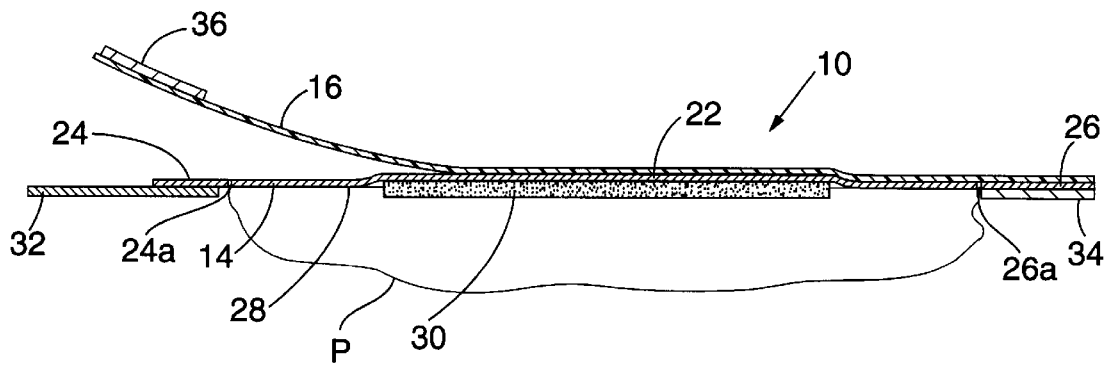
Figure 6:
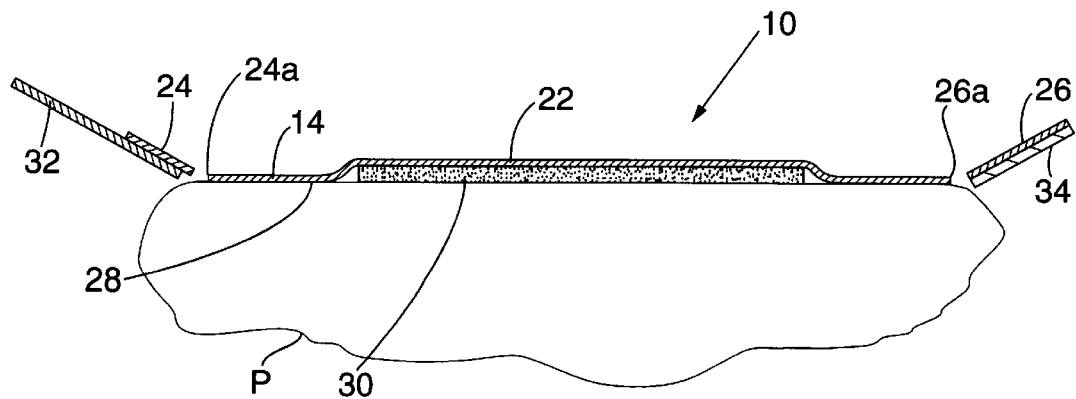

FIGS. 4–6 schematically show the application of a wound dressing 10 made in accordance with the present invention to a wound on a patient P. Referring first to FIG. 2, it will be appreciated that the first tab 32 is positioned outboard of the second tab 36 so that the user may more easily grab the first tab 32 without grabbing the second tab 36. In order to apply the wound dressing 10 to a wound on a patient P, the first tab 32 is gripped and pulled to facilitate separation of the layered upper urethane film 14/cover sheet 16 from the bottom carrier sheet 18. The first tab 32, which is not tacky, is interposed between the adhesive side 28 of the urethane film 14 and the release surface 20 on the carrier sheet 18 to promote the initial separation of the urethane film 14 from the carrier sheet 18. In response to the combination of the release surface 20 and the non-tacky first tab 32, pulling on the first tab 32 causes release of the urethane adhesive side 28 from the release surface 20, with the cover sheet 16 still adhering to the opposite side of the urethane film 14. The user may then grip the first tab 32 and, if necessary, the intermediate liner 34 to place the remaining combination of the urethane film 14/cover sheet 16 over the wound of a patient P as generally shown in FIG. 5. Once the adhesive side 28 of the middle portion 22 of the urethane film 14 contacts the skin, the adhesive side 28 sticks to the patient's skin. The user's fingers therefore need never come into contact with the adhesive layer 28 which will be placed against the patient's skin, thereby maintaining sterility of the wound dressing 10.

Moreover, the presence of the cover sheet 16 adjacent the thin urethane film 14 permits the wound dressing 10 to be placed adjacent the patent's skin and wound without stretching, wrinkling, or tearing the thin and relatively fragile urethane film 14. The cover sheet 16 is sufficiently flexible so as not to interfere with the ability of the urethane film 14 to conform to the contour of the patient P. The presence of cover sheet 16 also ensures the even application of the wound dressing 10 to the patient P surface by promoting evenly distributed tension between the cover sheet 16 and the urethane film 14, despite the tension created in response to manipulation of the first tab 32. This even release ensures that the urethane film 14 will not be distorted by excessive stresses exerted on any one region of the urethane film 14. It will thus be appreciated that the user must first release non-tacky tab 32 to overcome the attractive forces between the film 14 and the cover sheet 16.

Once in place, the adhesion of the urethane film 14 to the patient's skin is greater than the adhesion between the urethane film 14 and the cover sheet 16. Thus, as shown in FIG. 5, the second tab 36 can be pulled to separate the cover sheet 16 from the urethane film 14, thereby removing the cover sheet 16 and leaving the thin urethane film 14 adhering to the patient P. In order to promote the initial separation of the cover sheet 16 from the urethane film 14, it will be seen upon reference to FIG. 3, for example, that the non-tacky first tab 32 is adjacent to the non-tacky cover sheet 16. In contrast, the right end of the cover sheet 16 is in adjacent contact with the urethane film 14.

In the illustrated embodiment, the first tab 32 and the intermediate liner 34 are interposed between the adhesive side 28 of the urethane film 14 and the patient's skin to prevent the releasable end tabs 24, 26 from adhering to the patient's skin. Accordingly, the user may pull the left releasable end 24 (and first tab 32) and right releasable end 26 (and intermediate liner 34) away from the wound dressing 10 wherein the release means at the release lines 24a, 26a facilitates removal of releasable ends 24, 26 without disturbing the wound dressing 10 or the wound.

It should now be appreciated that the present invention, in accordance with certain objects of the invention, leaves a finished wound dressing 10 comprising a thin urethane film 14 and absorbent pad 30 on the wound area without stress areas or microbial contamination of the wound area.

In accordance with certain objects of the present invention, the tabs 32, 36 may bear an indicia indicating the order of use. The first tab 32 may bear an indicia indicating it is the first tab 32 in the two tab system. Similarly, the second tab 36 may contain an indicia indicating it is the second tab 36 in the two tab system. Indicia useful for marking on the two tab system that allow the error free application of the wound dressing 10 include color codes such as a blue first tab, a red second tab and a white intermediate liner, or numeric or alphanumeric references such as 1, 2, 3; I, II, III; A, B, C; Tab 1, Tab 2, Tab 3; First, Second, Third; Pull First, Pull Second, Pull Third; and the like. In accordance with other objects of the present invention, this two tab system allows the application of the wound dressing 10 using only one hand, particularly valuable for self-application to the hand or arm. Two hands are used to remove the carrier sheet 18, by holding the first tab 32. The hand holding the first tab 32 may then apply the wound dressing 10 and remove the flexible cover sheet 16 by pulling on the second tab 36. Finally, the ends 24, 26 of the urethane film 14 may be removed by separating along the release lines 24a, 26a.

The present invention also meets a long-felt need for a thin film wound dressing 10 which increases gas permeability which is necessary for increased healing rates and also patient comfort. This wound dressing 10 can be easily and safely applied to any type of wound or to an intravenous site. The transparent construction of the cover sheet 16 and urethane film 14 allow visual observation of the wound site during application and while on the patient P. The cover sheet 16 and tabs 32, 34 provide support for the wound dressing 10 until after application wherein the cover sheet 16 can then be removed easily using the two tab application system without distorting or stretching the film sheet affixed to the patient surface or skin. If necessary, the wound dressing 10 can be applied with one hand. The tabs may be optionally marked with indicia indicating the order of utilization, thereby permitting error free application on the first attempt even by the inexperienced.

FIGS. 7–11 schematically show a method for manufacturing the wound dressing 10. Generally, the wound dressing may be manufactured using rolls or webs of material and assembling such webs in successive layers to form the wound dressing 10. The various components are applied over each other in connected layers.

Figure 7:
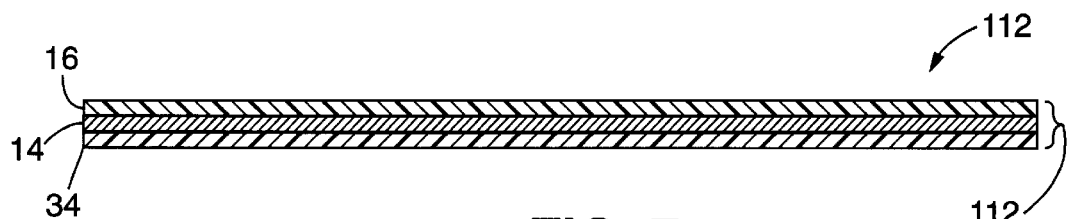
FIGS. 7–11 are sequential schematic views showing one embodiment of a method for manufacturing the wound dressing. Specifically.

Referring to FIG. 7, a web of sandwiched thin urethane film 14 may be made by forming or casting a urethane film 14, having the desired thickness, on a cover sheet 16 in a conventional manner. The thin urethane film 14 preferably has a thickness of less than about 1.0 mil, more preferably about 0.75 mil, and most preferably less than about 0.75 mil. It will, of course, be appreciated that, in other embodiments, the thickness of the urethane film 14 may be greater than about 1.0 mil. The cover sheet 16 is preferably made from a plastic material, but other conventional materials, such as paper, may be used. The formation process creates sufficient attractive forces to permit the urethane film and cover sheet to remain in adjacent contact during subsequent manufacturing steps while permitting a user to manipulate the film and to peel the film from the cover sheet. It is preferable that the urethane film and cover sheet be attached to each other without adhesives. However, in other embodiments, an adhesive may be used to attach the urethane film and cover sheet in which case, a preformed urethane film must be brought into adjacent contact with the cover sheet. An adhesive may be applied to the adhesive side 28 of the urethane film 14 so that an intermediate liner 34 may be attached to and cover the urethane film 14 for mechanical protection of the membrane 14 and to protect against contamination during subsequent storage and processing steps. The sandwiched urethane film 14 is typically formed into rolls or webs 112.

Figure 9:
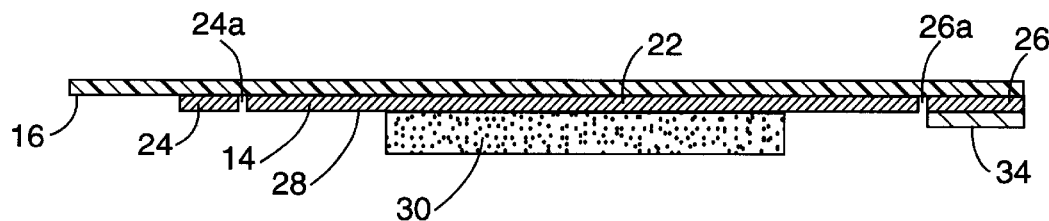

The triple-layered web 112 may subsequently be processed to separate portions of some of the layers as generally shown in FIG. 8. More specifically, the intermediate liner and the urethane film are cut and removed from the left end of the web 112 to form the releasable end 24. The tri-layered web 112 is subsequently scored and/or perforated at release lines 24a and 26a to form the left and right releasable ends 24, 26 and to properly size the middle portion 22 of the wound dressing 10. Referring to FIGS. 8–9, it will be seen that the remaining portion of the intermediate liner 34 now covers only the right releasable end 26 of the urethane film 14. The trimmed tri-layered web 112 is subsequently processed to receive the absorbent pad 30, the first tab 32 and the carrier sheet 18, as schematically shown in FIGS. 9–10.

Pre-sized absorbent material 30 may be inserted into the predetermined position on the urethane film 14. Specifically, the cut absorbent pad 30 are inserted at a predetermined and typically centered position relative to the release lines 24a, 26a defining the wound dressing 10. The adhesive side 28 of the urethane film 14 securely engages and holds the absorbent pad 30.

A web of the first tab 32 may be pressed into adjacent contact with the left releasable end 24 of the urethane film 14. More specifically, the right portion of the first tab 32 (as shown in the figures) is positioned so that it is substantially adjacent to or slightly outboard of the release line 24a. It is undesirable for the first tab 32 to be positioned on or inboard of the release line 24a because it will interfere with the separation of the left releasable end 24 from the wound dressing 10. The left portion of the first tab 32 is positioned outboard of the cover sheet 16. It will be appreciated that the left releasable end 24 is disposed between the cover sheet 16 and the first tab 32, but there is nothing between the cover sheet 16 and the left portion of the first tab 32.

Figure 11:
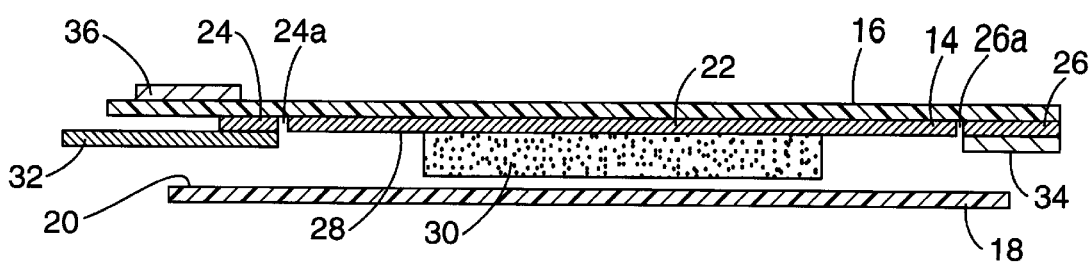

A web of the bottom carrier sheet 18 may be supplied so that the release side 20 is brought into contact with adhesive side 28 of the urethane film 14 as schematically shown in FIG. 11. It should now be appreciated that the carrier sheet 18 is releasably attached to the portions of the adhesive side 28 which are not covered by the absorbent pad 30, thereby securing the carrier sheet 18 and the urethane film 14 together. Referring to FIG. 1, it will be seen that the right portion of the carrier sheet 18 liner is slightly inboard of the right releasable end 26 of the cover sheet 16. The left portion of the carrier sheet 18 is substantially inboard of the first tab 32.

The second tab 36 may be attached to the top side of the cover sheet 16. It is preferable that the second tab 36 have an adhesive side 28 which is attached to the left end 24 of the cover sheet 16 as generally shown in FIG. 11, although other methods may apply the adhesive to the upper side of the cover sheet.

The size ranges of wound dressings 10 can vary from 0.20×1.0 inch to 18×18 inches. Preferred sizes of wound dressing 10 are 1"×3", 2"×3", 3"×4", 4"×5", 6"×8", 10"×12", 12"×18".

Although modifications and changes may be suggested by those skilled in the art, it is the intention of the inventor to embody within the patent warranted hereon all changes and modifications as reasonably and properly come within the scope of his contribution to the art.

We claim as our invention:

1. A non-stretching wound dressing for use with a patient comprising:

a cover sheet having top and bottom sides, a thin film sheet formed directly on the bottom side of the cover sheet, the film sheet having first and second ends and an adhesive side, a carrier sheet in adjacent contact with the adhesive side of the thin film sheet, a first gripping tab separate from and directly attached to one end of the thin film sheet and disposed between the film sheet and the carrier sheet for separating the carrier sheet from the film sheet with the cover sheet remaining affixed to the film sheet, and a second gripping tab separate from and directly attached to the top side of the cover sheet and at one end of the cover sheet so that pulling on the second gripping tab releases the cover sheet from the film sheet with the film sheet remaining in place on the patient.

2. The wound dressing as set forth in claim 1 wherein the thin film sheet has a thickness of about 1.0 mil.

3. The wound dressing as set forth in claim 1 wherein the thin film sheet has a thickness of less than about 1.0 mil.

4. The wound dressing as set forth in claim 3 wherein the thin film sheet has a thickness of about 0.75 mil.

5. The wound dressing as set forth in claim 1 wherein the thin film sheet has a thickness of less than about 0.75 mil.

6. The wound dressing as set forth in claim 1 comprising an intermediate liner separate from and directly attached to the adhesive side of the film sheet and disposed between the film sheet and the carrier sheet to promote removal of the film sheet and the carrier sheet, and to permit the wound dressing to be held by the first gripping tab and intermediate liner without contacting the thin film sheet.

7. The wound dressing as set forth in claim 6 wherein the second end of the film sheet comprises a releasable end so that the intermediate liner may be removed after the film sheet has been attached to the patient.

8. The wound dressing as set forth in claim 7 wherein the releasable end is formed by perforations.

9. The wound dressing as set forth in claim 7 wherein the releasable end is formed by scoring.

10. The wound dressing as set forth in claim 1 wherein the first end of the film sheet comprises a releasable end so that the first gripping tab may be removed after the film sheet has been attached to the patient.

11. The wound dressing as set forth in claim 10 wherein the releasable end is formed by perforations.

12. The wound dressing as set forth in claim 10 wherein the releasable end is formed by scoring.

13. The wound dressing as set forth in claim 1 wherein the thin film sheet is polyurethane.

14. The wound dressing as set forth in claim 1 comprising an absorbent material in adjacent contact with the adhesive side of the film sheet.

15. The wound dressing as set forth in claim 14 wherein the absorbent material comprises a medication.

16. A method of use of the wound dressing set forth in claim 1 comprising removing the carrier sheet from the wound dressing, applying the wound dressing to the patient such that the thin film sheet binds to the patient, removing the cover sheet from the thin film sheet using the first gripping tab thereby leaving the thin film sheet on the patient, and removing the first gripping tab.

17. A method for making a wound dressing comprising:

forming a thin film sheet directly on a cover sheet wherein the thin film sheet has a first side and first and second ends, adding an adhesive layer to a first side of the film sheet, adding a first gripping tab to the first end of the thin film sheet, and adding a carrier sheet to the adhesive side of the thin film sheet.

18. The method as set forth in claim 17 comprising adding an intermediate liner to the second end of the thin film sheet between the thin film sheet and the carrier sheet.

19. The method as set forth in claim 17 wherein the thin film sheet has a thickness of about 1.0 mil.

20. The method as set forth in claim 17 wherein the thin film sheet has a thickness of less than about 1.0 mil.

21. The method as set forth in claim 20 wherein the thin film sheet has a thickness of about 0.75 mil.

22. The method as set forth in claim 20 wherein the thin film sheet has a thickness of less than about 0.75 mil.

* * * * *